(12) United States Patent
Hamajima et al.

(10) Patent No.: US 6,506,959 B2
(45) Date of Patent: Jan. 14, 2003

(54) ABSORBENT ARTICLE

(75) Inventors: Mitsugu Hamajima; Mayumi Kimura; Yasuo Toyoshima; Minoru Nakanishi, all of Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/819,725

(22) Filed: Mar. 29, 2001

(65) Prior Publication Data
US 2001/0039406 A1 Nov. 8, 2001

(30) Foreign Application Priority Data

Apr. 11, 2000 (JP) ........................................ 2000-109939
Sep. 21, 2001 (JP) ........................................ 2000-287767

(51) Int. Cl.⁷ ................................................. A61F 13/15
(52) U.S. Cl. ........................ 604/367; 604/368; 604/378; 604/385.01
(58) Field of Search ................................ 604/368, 378, 604/367, 385.01

(56) References Cited

U.S. PATENT DOCUMENTS

| 5,637,105 A | 6/1997 | Tanaka et al. |
| 5,865,822 A | 2/1999 | Hamajima et al. |
| 6,068,619 A | 5/2000 | Hamajima et al. |

FOREIGN PATENT DOCUMENTS

| JP | 6218007 | 8/1994 |
| JP | 6287886 | 10/1994 |
| JP | 7132126 | 5/1995 |
| JP | 7184956 | 7/1995 |
| JP | 9156013 | 6/1997 |
| WO | 9614037 | 5/1996 |
| WO | 10508521 | 6/1998 |

Primary Examiner—Andy Falik
Assistant Examiner—Angela J Grayson
(74) Attorney, Agent, or Firm—Birch, Stewart, Kolasch & Birch, LLP

(57) ABSTRACT

An absorbent article comprising a liquid permeable topsheet, a liquid impermeable backsheet, and a liquid retentive absorbent layer is disclosed. The absorbent layer comprises a superabsorbent polymer and hydrophilic fiber or foam that does not swell with water or hydrophilic fiber or foam that has a water retention of 0.7 g/g or less when it is swollen with water and then dewatered by centrifugation. The absorbent article has a physiological saline fixing ratio of 90% or more when it absorbs 10 g of physiological saline and, after 5 minutes, is dewatered by centrifugation.

9 Claims, 4 Drawing Sheets

ABSORBENT ARTICLE

BACKGROUND OF THE INVENTION

The present invention relates to an absorbent article, such as a sanitary napkin, a disposable diaper, an adult incontinence pad, and a panty liner. More particularly, it relates to an absorbent article which has excellent absorption performance and is extremely comfortable while worn, causing little stuffiness.

Absorbent articles which prevent an internal humidity rise and stuffiness while worn have been proposed. For example, Japanese Patent Laid-Open Nos. 6-218007 and 7-132126 disclose absorbent articles comprising an absorbent member containing oven-dried pulp, a large quantity of a superabsorbent polymer, and a hygroscopic material, such as silica gel or lithium chloride, and a breathable backsheet.

Japanese Patent Laid-Open No. 10-508521 (WO96/14037) discloses an absorbent article having a combination of two breathable sheets as a backsheet so as to prevent liquid from oozing out through the backsheet.

However, these related techniques leave a discharged body fluid as non-fixed among paper or pulp fibers so that a body fluid, if discharged in a large amount, generates water vapor to cause stuffiness.

Japanese Patent Laid-Open No. 7-184956 proposes a sanitary napkin which prevents back-flow of an absorbed liquid from an absorbent member by using an absorbent member having a specific retention of simulated blood after equilibrium absorption and swell followed by centrifugation and a specific rate of transmission for simulated blood. Japanese Patent Laid-Open No. 6-287886 discloses a multilayer absorbent sheet comprising a surface layer (a layer with which a body fluid is brought into contact first) prepared from a mixed fiber containing bulky cellulose fiber by a papermaking technique and at least one base layer which is superposed on the surface layer. Japanese Patent Laid-Open No. 9-156013 proposes an absorbent sheet comprising a superabsorbent polymer and bulky cellulose fiber, the absorbent sheet having incorporated therein hydrophilic fine fiber or hydrophilic fine powder.

None of these related techniques makes a proposal on a structure which can markedly suppress water vapor generation thereby preventing stuffiness even when a large amount of a body fluid is discharged or should be absorbed.

SUMMARY OF THE INVENTION

An object of the present invention is to provide an absorbent article which hardly causes stuffiness and gives a comfort to a wearer even when a large amount of a body fluid is discharged and exhibits high absorptivity and excellent leakproofness.

Another object of the present invention is to provide an absorbent article which hardly causes stuffiness and gives a comfort to a wearer even when worn for a long time and exhibits high absorptivity and excellent leakproofness.

The present invention accomplishes the first object of the invention by providing, in its first aspect, an absorbent article comprising a liquid permeable topsheet, a liquid impermeable backsheet, and a liquid retentive absorbent layer, wherein the absorbent layer comprises a superabsorbent polymer and hydrophilic fiber or foam that does not swell with water or hydrophilic fiber or foam that has a water retention of 0.7 g/g or less when it is swollen with water and then dewatered by centrifugation, and the absorbent article has a physiological saline fixing ratio of 90% or more when it absorbs 10 g of physiological saline and, after 5 minutes, is dewatered by centrifugation.

The present invention also accomplishes the second object by providing, in its second aspect, an absorbent article comprising a liquid permeable topsheet, a liquid impermeable backsheet, and a liquid retentive absorbent layer, wherein the backsheet is breathable, and the absorbent article has a physiological saline fixing ratio of 90% or more when it absorbs 10 g of physiological saline and, after 5 minutes, is dewatered by centrifugation.

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
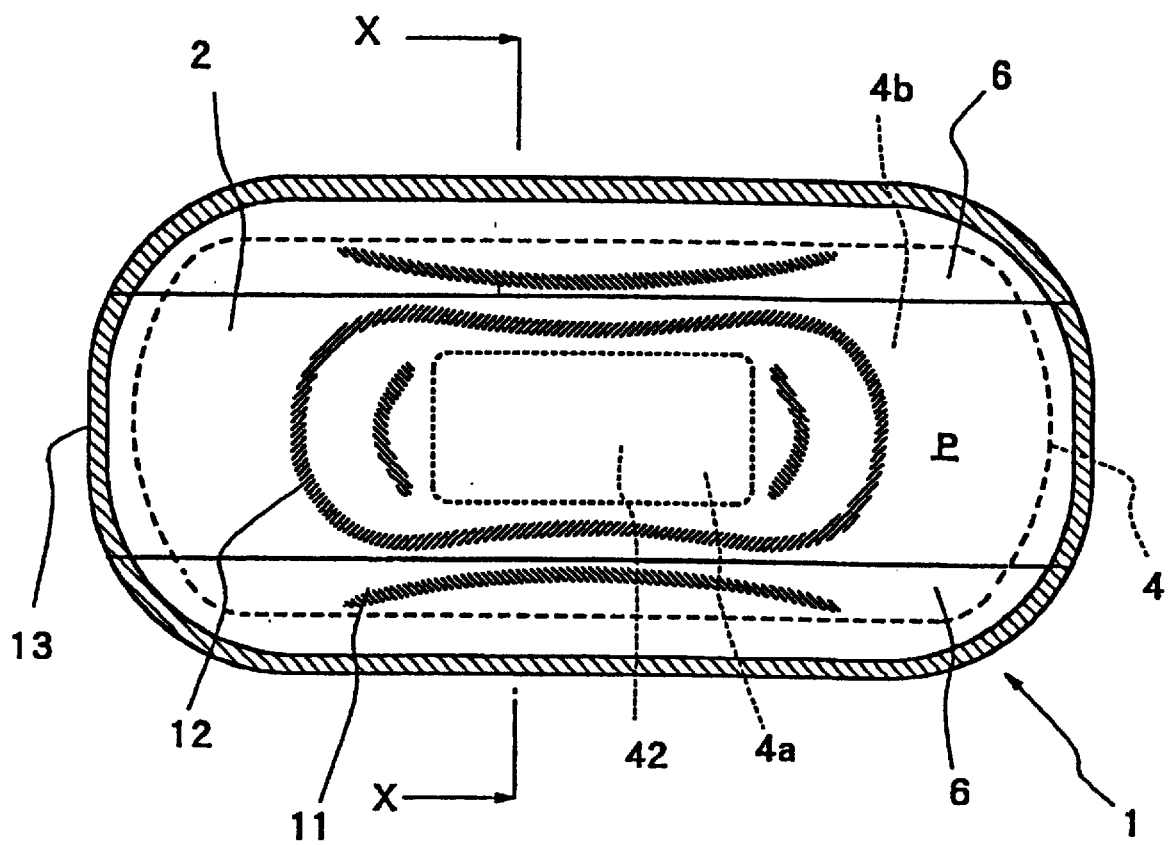
FIG. 1 is a plan view of a sanitary napkin as an embodiment of the absorbent article according to the present invention.
Figure 2:
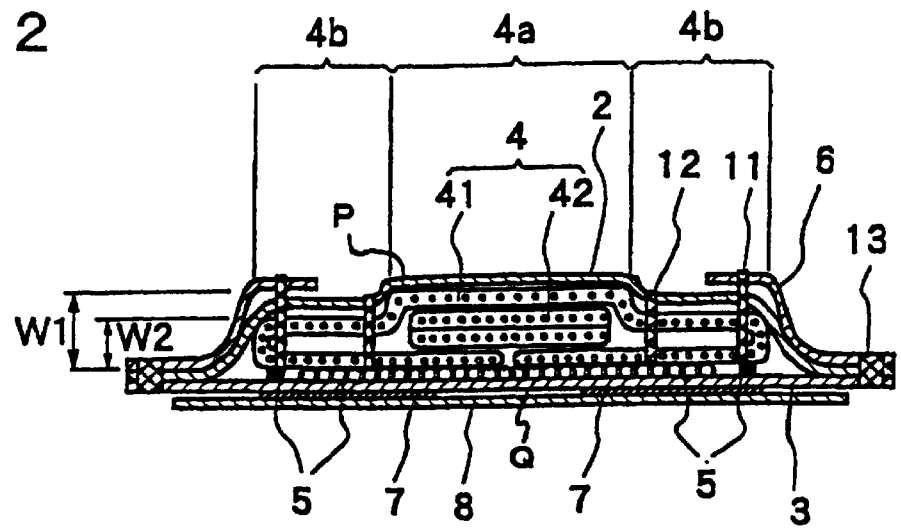
FIG. 2 is a schematic cross-section of the sanitary napkin shown in FIG. 1, taken along X—X line.

The present invention will hereinafter be described based on its preferred embodiment while referring to the accompanying drawings. FIG. 1 is a sanitary napkin as an embodiment of the absorbent article according to the present invention. FIG. 2 is a schematic cross-section of the sanitary napkin shown in FIG. 1, taken in the width direction along X—X line.

The sanitary napkin 1 according to this embodiment is substantially oblong and comprises a topsheet 2, which is a liquid permeable surface layer, a backsheet 3, which is a liquid impermeable leakproof layer, and an absorbent member 4, which is a liquid retentive absorbent layer interposed between the topsheet 2 and the backsheet 3.

The topsheet 2, the backsheet 3, and the absorbent member 4 each have an oblong shape and are joined into an unitary body with their longitudinal directions agreeing with each other.

The absorbent member 4 is adhered to the backsheet 3 with a hot-melt adhesive 5. A liquid impermeable leakproof sheet 6 is provided on both sides of the napkin 1 to form a leakproof portion covering both sides of the absorbent member 4. A pressure-sensitive adhesive 7 is applied on the lower side of the backsheet 3 in two bands to form a sticking area where to fix the napkin 1 to underwear. The sticking area is protected with a release sheet 8 until use.

The topsheet 2, the backsheet 3, and the leakproof sheet 6 each extend from the periphery of the absorbent member 4 and joined together at the extensions by heat sealing 13. The topsheet 2 and the leakproof sheet 6 are joined together by heat sealing 11 on both sides of the absorbent member 4. The topsheet 2 is joined to the upper surface of the absorbent member 4 by heat sealing 12.

The absorbent layer (absorbent member) 4 in the absorbent article according to the first aspect of the present invention comprises a superabsorbent polymer and hydrophilic fiber or foam that does not swell with water or hydrophilic fiber or foam that has a water retention of 0.7 g/g or less, preferably 0.5 g/g or less, when swollen with water followed by centrifugal dewatering.

The hydrophilic fiber or foam that does not swell with water can be of non-swelling resins, for example synthetic resins such as polyethylene, polypropylene, polyester, polyurethane, and composites of two or more thereof. Having a hydrophobic surface, these synthetic resins must be treated to be made hydrophilic (hydrophilic treatment). Hydrophilic treatment can be carried out by adhering a solution of a surface active agent to the synthetic resin fiber or foam by spraying or coating, or previously incorporating a hydrophilic surface active agent into the synthetic resin before molding so that the surface active agent can bleed on the surface of fiber or foam.

While any hydrophilic surface active agent having a hydrophilic group and a lipophilic group can be used in the hydrophilic treatment, anionic surface active agents and nonionic surface active agents having a large mole number of ethylene oxide added are preferred. Examples of preferred surface active agents are sulfosuccinic esters, alkyl ether sulfates, polyoxyethylene alkyl ethers, polyoxyethylene alkyl phenyl ethers, and glycerol fatty acid esters. Preferred of them are those capable of rendering the synthetic resin sufficiently hydrophilic when used in an amount of about 0.05 to 3% by weight. The surface active agents can be used either individually or as a mixture of two or more.

The hydrophilic fiber or foam having a water retention of 0.7 g/g or less, preferably 0.5 g/g or less, when swollen with water followed by centrifugation (hereinafter referred to as a centrifugal water retention) can be of materials that do not need a hydrophilic treatment, i.e., materials having a hydrophilic surface by itself. Such materials include crosslinked cellulose fiber having the cellulose molecules crosslinked intramolecularly or intermolecularly with an appropriate crosslinking agent, cellulose sponge, polynosic rayon fiber having improved crystallinity, polyvinyl alcohol fiber, polyvinyl alcohol sponge, acrylic fiber, and acrylic sponge. The crosslinked pulp fiber obtained by crosslinking wood pulp comprising cellulose is preferred for the economical consideration.

Hydrophilic fiber or foam having a centrifugal water retention exceeding 0.7 g/g would reduce its elastic modulus on liquid absorption, allowing the liquid to remain in the interstices among fibers or in voids. It would follow that the remaining liquid generates water vapor to increase the humidity in the internal atmosphere. The method of measuring a centrifugal water retention of hydrophilic fiber or foam will be described in detail in Examples hereinafter given.

General chemical pulp of softwood pulp, hardwood pulp, etc. has a centrifugal water retention of about 1 to 2 g/g. The hydrophilic fiber or foam having a centrifugal water retention of 0.7 g/g or less will sometimes be referred to as "low-swelling hydrophilic fiber or foam".

The crosslinking agent used to crosslink cellulose preferably includes N-methylol compounds such as dimethylolethyleneurea and dimethylolhydroxyethyleneurea, polycarboxylic acids such as citric acid, tricarballylic acid, and butanetetracarboxylic acid, polyglycidyl ether compounds, and dialdehyde compounds.

The absorbent layer (absorbent member) 4 in the absorbent article according to the first aspect of the present invention comprises a superabsorbent polymer in addition to the above-described non-swelling or low-swelling hydrophilic fiber or foam. Most of a liquid having passed through the topsheet is absorbed and held in the superabsorbent polymer without being allowed to remain among fibers or in voids of foam. As a result, generation of water vapor from the liquid can be reduced thereby effectively preventing a humidity rise in the internal environment.

It is preferred that the superabsorbent polymer be capable of absorbing and holding 20 times as heavy a body liquid as its own weight and also capable of gelling. Examples of preferred superabsorbent polymers are starch, crosslinked carboxymethylated cellulose, homo- or copolymers of acrylic acid or an alkali metal salt of acrylic acid, polyacrylic acid or a salt thereof, and polyacrylic acid salt graft polymers. The polyacrylic acid salt is preferably a sodium salt.

It is also preferred that the superabsorbent polymer quickly takes up and retains a body fluid from the interstices among fibers or voids of foam and also keeps its surface dry after absorption and swelling with the body fluid and therefore hardly releases water vapor and does not hinder migration of the body fluid through polymer particles even after absorption and swelling. Such functions are difficult to obtain if the polymer has a uniform crosslinked structure. Therefore, it is desirable for the superabsorbent polymer to have a crosslinking density gradient.

A superabsorbent polymer, for example, a polyacrylic acid salt, with a crosslinking density gradient can be obtained by allowing the polymer to react with a crosslinking agent capable of reacting with the functional group of the polyacrylic acid salt (hereinafter "polymer crosslinking agent") to cause the polymer surface to crosslink. The polymer crosslinking agent preferably includes compounds having two or more functional groups capable of reacting with a carboxyl group, such as polyglycidyl ethers (e.g., ethylene glycol diglycidyl ether, polyethylene glycol diglycidyl ether, and glycerol triglycidyl ether), polyols (e.g., glutaraldehyde and glyoxal), and polyamines (e.g., ethylenediamine).

It is preferred that the superabsorbent polymer particles be non-spherical. Upon absorption and swelling with a body fluid, spherical superabsorbent polymer particles are liable to be re-arranged or come into close contact with each other to reduce voids among themselves, which easily leads to a gel blocking phenomenon. Non-spherical particles effectively prevent such a gel blocking phenomenon, keeping the ability to quickly and sufficiently absorb a body fluid.

Non-spherical superabsorbent polymer particles can be prepared by, for example, a method comprising grinding a superabsorbent polymer obtained by bulk polymerization, a method comprising allowing polymer particles to agglomerate through contact reaction in the presence of a polymer crosslinking agent into amorphous secondary particles, a method relying on choice of a dispersant to be used in the polymer production.

The superabsorbent polymer is used in combination with hydrophilic fiber or foam. The manner of the superabsorbent polymer's being combined with the hydrophilic fiber or foam is not particularly restricted. For example, the polymer can be disposed in a layer(s) or uniformly distributed in an aggregate of hydrophilic fiber or in hydrophilic foam by scattering. It is preferred that the superabsorbent polymer be three-dimensionally dispersed in a hydrophilic fiber aggregate or foam to secure a large contact area between the fiber or foam with the superabsorbent polymer. As a result, the body fluid having passed through the topsheet can be rapidly absorbed by the superabsorbent polymer without staying among fibers or in voids of foam to efficiently prevent a humidity rise.

The language "three-dimensionally dispersed" as used herein is intended to mean that the absorbent polymer is not in the form of lines or layers in a fiber aggregate or foam but is dispersed in not only the planar direction but the thickness direction in a fiber aggregate or foam.

The superabsorbent polymer preferably has a centrifugal physiological saline retention of 25 g/g or more, particularly 30 g/g or more. The method of measuring the centrifugal physiological saline retention will be described in Examples.

The proportion of the non-swelling or low-swelling hydrophilic fiber or foam in the absorbent layer (absorbent member) 4 is preferably 30 to 70% by weight, still preferably 40 to 70% by weight.

With the proportion of the non-swelling or low-swelling hydrophilic fiber or foam being within the above range, the absorbent article can have an increased liquid fixing ratio, and the shape stability of the absorbent member and the polymer fixing properties are improved.

The non-swelling fiber or foam and the low-swelling fiber or foam can be used in combination. In this case, the total amount of the fibers or foams preferably falls within the above range.

The proportion of the superabsorbent polymer in the absorbent layer (absorbent member) 4 is preferably 30 to 70% by weight, still preferably 35 to 60% by weight. In this range, the absorbent article has a high liquid fixing ratio, and it is easier to design an absorbent article so that the absorbent member may have shape retention against a wearer's movement and that the polymer may be immobilized in the absorbent member.

The weight ratio of the non-swelling hydrophilic fiber or foam and/or low-swelling hydrophilic fiber or foam to the superabsorbent polymer in the absorbent layer (absorbent member) 4 is preferably 3/7 to 7/3.

Materials of the absorbent layer (absorbent member) 4 of the absorbent article according to the second aspect of the invention include, but are not limited to, the above-described non-swelling or low-swelling hydrophilic fiber or foam and superabsorbent polymer. Fiber or foam having a centrifugal water retention exceeding 0.7 g/g can also be employable.

In this absorbent article, because the liquid impermeable backsheet has water vapor permeability, water vapor generated from the absorbed but not fixed body fluid in the absorbent member dissipates through the backsheet. As a result, the amount of the non-fixed liquid reduces, which means that the available amount of the hydrophilic fiber or foam can be increased. This is why the material of the absorbent member is not limited to fiber or foam having a centrifugal water retention of 0.7 g/g or less.

The absorbent article (e.g., the sanitary napkin 1) of the present invention has a physiological saline fixing ratio of 90% or more, preferably 93% or more, when it absorbs 10 g of physiological saline and, after 5 minutes, is dewatered by centrifugation (the physiological saline fixing ratio will hereinafter be simply referred to as a liquid fixing ratio).

The liquid fixing ratio is preferably as high as possible. The upper limit is 100%. The method of measuring the liquid fixing ratio will be described in Examples.

If the liquid fixing ratio is less than 90%, much water vapor generates from the absorbent article to cause stuffiness. Additionally, the absorbent article having a liquid fixing ratio of 90% or higher does not release liquid once absorbed and held, thereby effectively preventing leakage.

While not limiting, a liquid fixing ratio of 90% or higher is preferably achieved by making the absorbent member 4 of the aforementioned hydrophilic fiber or foam and the aforementioned superabsorbent polymer and letting a body fluid having passed through the topsheet be quickly absorbed by the superabsorbent polymer without allowing it to stay among the fibers or in the voids of the foam. It is still preferred that the body fluid having passed through the topsheet be swiftly absorbed from the surface of the absorbent member and be diffused all over the superabsorbent polymer particles inside the absorbent member.

Specifically, it is desirable for an aggregate of the hydrophilic fiber or the hydrophilic foam near the superabsorbent polymer particles to have a Klemm's water absorption of 40 mm or more, particularly 50 mm or more, at 1 minute as measured for physiological saline in accordance with JIS P8141. Such a high diffusing property can be obtained by increasing the specific surface area of the fiber aggregate or foam by proper selection of the fiber diameter, the pore diameter, and the like.

It is also preferred to make a diffusion gradient in the hydrophilic fiber aggregate or the hydrophilic foam from the surface of the absorbent member to the vicinity of the superabsorbent polymer so that the liquid may diffuse more easily in the vicinity of the superabsorbent polymer than in the surface of the absorbent member.

Diffusing properties of, for example, hydrophilic fiber obtained by hydrophilic treatment of non-swelling synthetic fiber can be improved by reducing the fiber diameter to increase the specific surface area of the fiber. In this case, a preferred average fiber diameter is 20 $\mu$m or smaller, particularly 0.1 to 10 $\mu$m. A fiber aggregate comprising fibers with such an average diameter preferably includes melt-blown nonwoven fabric that can have very fine fibers. Superabsorbent polymer particles can be scattered while fibers blown from a melt-blowing nozzle are built up to obtain a web in which the polymer particles are three-dimensionally distributed among the fibers.

The absorbent layer (absorbent member) having higher liquid diffusing properties in the vicinity of the superabsorbent polymer than in the surface thereof is preferably one comprising a surface fiber layer, which forms the surface in contact with the topsheet, and an inner fiber layer, which is disposed on the back side of the surface fiber layer, wherein the inner fiber layer contains the superabsorbent polymer or is in contact with the superabsorbent polymer, and the surface fiber layer having a lower Klemm's water absorption than the inner fiber layer.

The inner fiber layer preferably has a Klemm's water absorption of 40 mm or more, particularly 50 mm or more, and the surface fiber layer preferably has a Klemm's water absorption of less than 40 mm, particularly 5 to 35 mm.

With a difference in Klemm's water absorption between the surface fiber layer and the inner fiber layer and with a diffusion gradient, especially where the Klemm's water absorption of the surface fiber layer is less than 40 mm, and that of the inner fiber layer is 40 mm or more, the body fluid absorbed by the surface fiber layer can be quickly led to the superabsorbent polymer in the inner fiber layer through capillaries and absorbed thereby.

The inner fiber layer may be a sheet of nonwoven fabric having the superabsorbent polymer particles dispersed therein or two sheets of nonwoven fabric having the superabsorbent polymer particles therebetween.

Where the absorbent member is made up of two kinds of hydrophilic fibers having different diameters in such a manner that the diameter of the fibers in the vicinity of the superabsorbent polymer is 0.1 to 10 μm while that of the fibers making the surface of the absorbent member is 10 to 100 μm, the ratio of the fine fibers to the thick fibers is preferably 3/7 to 9/1 by weight.

An absorbent member in which the hydrophilic fiber or foam exhibits higher liquid diffusing properties in the vicinity of the superabsorbent polymer than in the surface thereof can be obtained by, for example, superposing nonwoven fabric (surface fiber layer) made of thick hydrophilic fibers prepared by hydrophilic treatment of non-swelling synthetic fibers on a composite sheet (inner fiber layer) composed of the above-described melt-blown nonwoven fabric made of fine fibers and superabsorbent polymer particles held among the fibers. The nonwoven fabric used as a surface fiber layer preferably includes spun-bond nonwoven fabric, heat roll nonwoven fabric, suction heat-bond nonwoven fabric, and so forth which are made of synthetic fibers, such as polyethylene, polypropylene, polyester, polyurethane, and composites thereof, having been rendered hydrophilic by hydrophilic treatment and having a diameter of 10 to 100 μm.

Where hydrophilic fiber having a centrifugal water retention of 0.7 g/g or less is used, the liquid diffusing properties can be improved preferably by moderately adjusting the fiber density of the fiber aggregate or adding a small proportion of very fine pulp fibers having a large specific surface area, such as hardwood pulp.

A diffusion gradient can be provided by increasing the fiber density of the fiber aggregate in the vicinity of the superabsorbent polymer over that in the surface of the absorbent member or incorporating a small proportion of very fine pulp fibers having a large specific surface area, such as hardwood pulp, into the vicinity of the superabsorbent polymer.

An absorbent member comprising the hydrophilic fiber having a centrifugal water retention of 0.7 g/g or less and the superabsorbent polymer can be produced in either a dry process or a wet process. In a dry process, the hydrophilic fiber is air-laid into a web, and the superabsorbent polymer particles are scattered thereon; or the hydrophilic fiber and the superabsorbent polymer particles are built up into a web while being mixed together. In order to improve dry and wet strength of the web, thermally bonding fiber, such as polyethylene fiber, polypropylene fiber, polyester fiber or a composite thereof, may be mixed into the hydrophilic fiber, and the resulting web is thermally treated to fuse-bond the thermally bonding fibers to each other. A binder, such as an acrylic ester copolymer, an acrylic ester-vinyl acetate copolymer, and an ethylene-vinyl acetate copolymer, can be applied to the web by spraying and dried to make the web stronger in both dry and wet states.

In a wet process, an aqueous slurry of the hydrophilic fiber is made into an web on a papermaking wire, and the superabsorbent polymer is scattered on the web before it is dried in a drier. The scattered superabsorbent polymer manifests tack on absorbing water from the wet web. Another web of the hydrophilic fiber is superposed thereon, and the laminate is dried in a drier to obtain sheeting in which the superabsorbent polymer is adhered to the hydrophilic fiber and dried. The wet process is preferred; for the fibers in the vicinities of the polymer particles gather by the tack development of the polymer followed by drying to gain in density, resulting in formation of a diffusion gradient.

A diffusion gradient can also be made by combining hydrophilic fiber having a centrifugal water retention of 0.7 g/g or less and non-swelling synthetic fiber having been subjected to hydrophilic treatment.

It is preferred that the absorbent layer (absorbent member) 4 has a $V_1/V_0$ ratio of 1 g/cm$^3$ or higher, wherein $V_0$ is the effective volume (cm$^3$) of the absorbent layer, and $V_1$ is the amount (g) of physiological saline retained when the absorbent layer is swollen with physiological saline and dewatered by centrifugation. The ratio of the physiological saline retention $V_1$ to the effective volume $V_0$, hereinafter referred to as a retention-to-volume ratio P, is still preferably 1.5 g/cm$^3$ or more. The more high, the more preferred.

With the retention-to-volume ratio P being 1 g/cm$^3$ or more, the absorbent layer (absorbent member) has sufficient absolute retentivity enough to effectively prevent a body fluid from remaining in the interstices among the fibers of the fiber aggregate or in the voids of the foam. As a result, the liquid is more effectively prevented from leaking or dissipating as water vapor.

The term "effective volume ($V_0$)" as used for the absorbent layer denotes the volume of the absorbent layer under a load of 2.5 g/cm$^2$, which is obtained by multiplying the thickness of the absorbent layer under that load by the effective area (flat area) of the absorbent layer. The physiological saline retention ($V_1$), the amount of physiological saline left after swelling followed by centrifugation, means the amount (g) of physiological saline that can be fixed completely within the absorbent layer. The method for measuring $V_1$ will be described later in detail. With the retention-to-volume ratio P being 1 g/cm$^3$ or more, the body fluid absorbed in the effective volume $V_0$ can be absorbed and held in the superabsorbent polymer, provided that the body fluid flows ideally in the absorbent layer.

While dependent on the use or product size of an absorbent article, the physiological saline retention $V_1$ of, for instance, a sanitary napkin is preferably such that the physiological saline retention $V_1$ per flat unit area (m$^2$) of the absorbent member is 1000 g/m$^2$ or more, particularly 2000 g/m$^2$ or more.

The absorbent layer (absorbent member) 4 preferably has a thickness of 2.5 mm or smaller. Within this thickness, discomfort while use can be minimized, and the limited unit volume of the absorbent article limits the amount of water vapor produced from the absorbent member thereby reducing or preventing a humidity rise or stuffiness while worn. In view of balance with absorptivity, the lower limit of the thickness of the absorbent layer is about 0.5 mm. The thickness of the absorbent layer is measured under a load of 2.5 g/cm$^2$.

As shown in FIGS. 1 and 2, the absorbent member 4 of the sanitary napkin 1 according to the present embodiment has a thicker portion in the area where a body fluid is to be discharged. Specifically, the thicker portion 4a is provided in the central portion of the napkin 1 where blood is to be discharged, and it forms an upward protrusion on a wearer-facing side P of the napkin 1.

The thickness W1 of the thicker portion 4a is preferably 1.5 to 2.5 mm. The thickness W2 of the portion 4b surrounding the thicker portion 4a is preferably 0.5 to 2.0 mm. The ratio of W1 to W2 (W1/W2) is preferably 1.5 to 4.

Since the absorbing material is thus localized in the discharge portion, the discharged body fluid concentrates in the central portion without spreading. As a result, the area wetted with the body fluid, from which water vapor generates, is limited. Since the surrounding portion is thinner than the central portion, the humidity and temperature can be dissipated more effectively.

The area of the thicker portion 4a is preferably 10 to 50% based on the total area of the wearer-facing side P of the absorbent member 4. The shape and dimensions of the thicker portion 4a are decided appropriately according to the use of the absorbent article. For example, the thicker portion 4a is preferably rectangular with its longitudinal direction agreeing with that of the napkin. The size of the thicker portion 4a, in a sanitary napkin of regular size for daytime use (product length: 180 to 260 mm), is preferably 20 to 50 mm in width and 60 to 150 mm in length and, in a sanitary napkin of bigger size for nighttime use (product length: 260 to 350 mm), is preferably 20 to 50 mm in width and 100 to 250 mm in length.

It is preferred that the liquid impermeable backsheet be breathable or permeable to water vapor. Breathable backsheet (hereinafter referred to as "moisture permeable backsheet") allows water vapor of a wearer's perspiration due to her exercise, etc. to escape efficiently. With this effect combined with the absorbent member's capability of absorbing and fixing most of the discharged body fluid, an increase in humidity and resultant stuffiness during use can be prevented effectively. In addition, the preferred small thickness of the absorbent member as described above also facilitates dissipation of raised temperature in the internal environment thereby keeping the internal temperature and humidity comfortable to a wearer.

For preventing an internal humidity rise in use, the breathability of the backsheet 3 is preferably such that the moisture vapor transport rate as specified in JIS Z0208 is 0.3 g/(100 cm$^2$·hr) or more, particularly 0.7 g/(100 cm$^2$·hr) or more, especially 1.0 to 5.0 g/(100 cm$^2$·hr) as measured in the method specified.

The moisture permeable backsheet can be of any material having both waterproofness and breathability. Useful materials include a porous film obtained by molding a molten resin composition comprising a hydrophobic thermoplastic resin (e.g., polyethylene, polypropylene or a mixture thereof) and a fine filler (e.g., calcium carbonate or barium sulfate) into sheeting, which is stretched uniaxially or biaxially; sized waterproof paper; nonwoven fabric made of fine hydrophobic thermoplastic resin fiber obtained by, e.g., melt-blowing; and a composite sheet composed of two or more of such a porous film, waterproof paper, and nonwoven fabric.

Waste body fluids, such as urine, usually has a surface tension of 50 to 60 mN/m. While the surface tension of blood is about 50 mN/m, sanitary napkins infrequently receive blood having a very low surface tension. Where disposable diapers contain materials having been treated with a surface active agent to have increased hydrophilicity as a surfacing material or an absorbing material, the surface active agent sometimes dissolves in a large amount of urine to reduce the surface tension of urine.

In such a case a body fluid having a very low surface tension is absorbed by an absorbent member, it tends to penetrate through fine pores of a moisture-permeable leakproof backsheet and ooze out.

The technique taught in Japanese Patent Laid-Open No. 10-508521 supra is to prevent liquid from oozing through a moisture permeable backsheet by designing the physical thickness or structure of the moisture permeable backsheet. Use of two backsheets according to this technique requires complicated equipment for processing stock sheets, which invites an increase of cost. Further, when blood of low surface tension is discharged, it is likely to ooze out. Furthermore, when a large amount of a body fluid is excreted, water vapor generates to cause stuffiness.

The moisture permeable backsheet preferably has a wetting tension of 37 mN/m or less, particularly 35 mN/m or less, so as to prevent a discharged body fluid from oozing out through the fine pores thereof even where the body fluid has an extremely low surface tension. The terminology "wetting tension" as used for the backsheet means the lowest surface tension of a test liquid that is dropped on a sample sheet and does not ooze from the back side of the sheet. The method of measurement will be described in detail in Examples.

When, for example, a porous stretched film of a thermoplastic resin containing an inorganic filler, such as calcium carbonate or barium sulfate, is used as a backsheet, such a low wetting tension can be obtained by using a lipophilic dispersant of lower surface energy for uniformly dispersing the inorganic filler in the thermoplastic resin. The moisture permeable backsheet can be a single sheet, which is preferred, or made of a plurality of sheets.

The topsheet 2 can be of any type customarily used in absorbent articles, such as nonwoven fabric, perforated film, and the like. Preferred is perforated nonwoven fabric made of polyethylene fiber, polypropylene fiber, polyester filer, polyethylene-polypropylene conjugate fiber, polyethylene-polypropylene conjugate fiber, or a mixed fiber thereof While a perforated film comes into contact with a wearer's skin with a large contact area and has no breathability (air permeability) in its non-perforated area, perforated nonwoven fabric shows breathability in its non-perforated area through the interstices among fibers. By making three-dimensional perforations through nonwoven fabric, breathing also occurs through the inner wall of the perforations. Therefore, perforated nonwoven fabric as a topsheet effectively prevents a humidity rise and resultant stuffiness in the internal environment while the absorbent article is worn.

Compared with a perforated film, nonwoven fabric as a topsheet has been considered disadvantageous in that an absorbed liquid is liable to flow back and leak, but this drawback is eliminated in the present invention because most of the body fluid absorbed in the absorbent layer is fixed in the superabsorbent polymer and hardly flows back and oozes on the surface of the topsheet.

The present invention is applicable to not only sanitary napkins as specifically referred to above but disposable diapers, adult incontinence pads, panty liners, and like absorbent articles.

The present invention will now be illustrated in greater detail with reference to Examples and Comparative Examples. Unless otherwise noted, all the percents and ratios are by weight.

1) Preparation of Superabsorbent Polymer A

In a 500 ml four-necked round flask equipped with a stirrer, a reflux condenser, a dropping funnel, and a tube for introducing nitrogen gas were put 230 ml of cyclohexane and 1.4 g of sorbitan monostearate (Leodor SPS-12, available from Kao Corp.) and stirred to prepare a uniform solution. Separately, 30 g of an acrylic acid monomer was neutralized with 13.4 g of sodium hydroxide dissolved in 39 g of water in a conical flask to prepare an aqueous monomer solution having a monomer concentration of 45% (water content: 55%).

In the aqueous monomer solution was dissolved 0.1 g of potassium persulfate. The monomer solution was added dropwise into the four-necked round flask containing cyclohexane, etc. in a nitrogen atmosphere. The mixture was heated to 70 to 75° C. to initiate polymerization. The reaction system was refluxed while azeotropically dehydrating to adjust the water content of the polymer (as suspended in cyclohexane) at 35%. A solution of 0.03 g of ethylene glycol diglycidyl ether in 1 ml of water was added thereto at 73° C. and, after the mixture was kept at that temperature for 2 hours, cyclohexane was removed. The resulting polymer was dried at 80 to 100° C. under reduced pressure to obtain superabsorbent polymer A. Superabsorbent polymer A had a crosslinking density gradient on its surface, was amorphous, and had a centrifugal physiological saline retention of 33 g/g.

2) Preparation of Superabsorbent Polymer B

In the same four-necked round flask as used above were put 230 ml of cyclohexane and 1.94 g of ethyl cellulose (N-200, available from Hercules Far-East), followed by stirring to prepare a uniform solution. The same aqueous monomer solution as used above was prepared.

The solution in the four-necked round flask was heated to 70 to 75° C., and the monomer solution was added thereto dropwise over 1.5 hours in a nitrogen atmosphere. The mixture was maintained at 70 to 75° C. for 0.5 hour to complete polymerization. Cyclohexane was removed, and the resulting polymer was dried at 80 to 100° C. under reduced pressure to obtain superabsorbent polymer B. Superabsorbent polymer B had no crosslinking density gradient, was spherical, and had a centrifugal physiological saline retention of 28 g/g.

3) Preparation Absorbent Member A

A mixed (1:1) surface active agent consisting of an alkyl phosphate and a sorbitan fatty acid ester was applied to core/sheath type conjugate fiber consisting of polyethylene as a sheath and polyester (polyethylene terephthalate) as a core and having a fiber diameter of 15 $\mu$m (2.2 dtex) to obtain non-swelling hydrophilic fiber having the surface active agent adhered in an amount of 0.4%. The fiber was made into suction heat-bond nonwoven fabric having a Klemm's water absorption of 10 mm and a basis weight of 20 g/m$^2$, which was used as a surface fiber layer.

Linear low-density polyethylene (an ethylene-1-octene copolymer available from Mitsui Petrochemical Industries, Ltd.) was mixed with 1% of polyoxyethylene sorbitan monolaurate (6 mol of ethylene oxide added; available from Kao Corp.) as a hydrophilic surface active agent and made into non-swelling fibers having an average diameter of 8 $\mu$m by a melt blowing technique, which were built up on the suction heat-bond nonwoven fabric (surface fiber layer) to form an inner fiber layer having a basis weight of 30 g/m$^2$. The melt-blown nonwoven fabric formed on the suction heat-bond nonwoven fabric had a Klemm's water absorption of 55 mm. Superabsorbent polymer A was scattered on the melt-blown nonwoven fabric (inner fiber layer) in an amount of 40 g/m$^2$, and the same linear low-density polyethylene containing the hydrophilic surface active agent as used above was melt-blown into fibers having an average diameter of 8 $\mu$m and built-up on the scattered polymer particles in an amount of 30 g/m$^2$ to obtain polymer sheet A having a total basis weight of 120 g/m$^2$.

Separately, the same linear low-density polyethylene fiber containing the hydrophilic surface active agent was melt-blown into fibers (average fiber diameter: 8 $\mu$m). While the melt-blown fibers were being built up on a net, they were mixed with an equal weight of superabsorbent polymer A to prepare polymer sheet B having a total basis weight of 80 g/m$^2$ (of which the superabsorbent polymer A had a basis weight of 40 g/m$^2$).

Polymer sheet A was cut into a piece having a size of 140 mm by 175 mm, and polymer sheet B was cut into two pieces each having a size of 35 mm by 80 mm. Both edges in the width direction of the cut sheet of polymer sheet A were folded back with the suction heat-bond nonwoven fabric outward to have the structure shown by numeral 41 in FIG. 2, with two cut sheets of polymer sheet B being disposed in the center of the folded polymer sheet A as indicated by numeral 42 in FIG. 2. The resulting structure was designated absorbent member A.

4) Preparation of Absorbent Member B

Polymer sheet A was cut into a size of 140 mm by 175 mm, and polymer sheet B was cut into a size of 70 mm by 175 mm. The cut sheet of polymer sheet A was folded with the cut sheet of polymer sheet B being interposed in the fold in the same manner as in the preparation of absorbent member A to obtain absorbent member B.

5) Preparation of Absorbent Member C

A hundred grams of chemical wood pulp having a centrifugal water retention of 1.1 g/g (NB-416L, available from Wyerhauser Paper Co.) was dispersed in 1000 g of an aqueous solution containing 5% of dimethyloldihydroxyethyleneurea (Sumitex Resin NS-19, available from Sumitomo Chemical Co., Ltd.) as a crosslinking agent and 3% of a metallic catalyst (Sumitex Accelerator X-110, available from Sumitomo Chemical Co., Ltd.). The dispersion was concentrated until the amount of the aqueous crosslinking agent solution was reduced to 200% based on the wood pulp. The concentrate was heated in an electric drier at 135° C. for 10 minutes to intermolecularly or intramolecularly crosslink the cellulose to obtain crosslinked pulp A. Crosslinked pulp A had a centrifugal water retention of 0.35 g/g.

A hundred grams of hardwood pulp LBKP having a centrifugal water retention of 1.3 g/g (Prime Albeat Handwood, available from Wyerhauser Paper Co.) was crosslinked in the same manner as described above to obtain crosslinked pulp B. Crosslinked pulp B had a centrifugal water retention of 0.45 g/g.

Crosslinked pulp A and superabsorbent polymer A were mixedly air-laid at a mixing ratio of 1:1 into a web having a basis weight of 90 g/m$^2$. An acrylic ester copolymer (Movinyl 710, available from Hoechst Gosei K.K.) was sprayed on the web in an amount of 10 g/m$^2$ on a solid basis, and the sheet was compressed and dried to obtain polymer sheet C having a total basis weight of 100 g/m$^2$. The polymer sheet C is to be used as an inner fiber layer. Polymer sheet C had a Klemm's water absorption of 43 mm.

Crosslinked pulp A, crosslinked pulp B, and superabsorbent polymer A were mixedly air-laid at a mixing ratio of 4:1:5 into a web having a basis weight of 90 g/m$^2$. An acrylic ester copolymer (Movinyl 710, available from Hoechst Gosei K.K.) was sprayed on the web in an amount of 10 g/m$^2$ on a solid basis, and the sheet was compressed and dried to obtain polymer sheet D having a total basis weight of 100 g/m$^2$. Polymer sheet D had a Klemm's water absorption of 50 mm.

Polymer sheet C (inner fiber layer) and the same suction heat-bond nonwoven fabric (surface fiber layer) as used in the preparation of absorbent member A (Klemm's water absorption: 10 mm; basis weight: 20 g/m$^2$) were superposed on each other. The resulting laminate was cut into a size of 140 mm by 175 mm. Polymer sheet D was cut into a size of 35 mm by 80 mm. The cut sheet of the laminate was folded with the suction heat-bond fabric outward, and the cut sheet of polymer sheet D was interposed in the center of the fold in the same manner as in the preparation of absorbent member A to obtain absorbent member C.

6) Preparation of Absorbent Member D

An aqueous slurry containing crosslinked pulp A and polyvinyl alcohol fiber.

Chemical wood pulp having a centrifugal water retention of 1.1 g/g (NB-416L, available from Wyerhauser Paper Co.) and superabsorbent polymer A were mixed in air at a ratio of 1:1 and laid down to obtain a web having a basis weight of 90 g/m². An acrylic ester copolymer (Movinyl 710, available from Hoechst Gosei) was sprayed onto the web in an amount of 10 g/m² on a solid basis and dried to obtain polymer sheet H having a total basis weight of 100 g/m². Polymer sheet H had a Klemm's water absorption of 40 mm.

A sheet of 140 mm by 175 mm and two sheets of 35 mm by 80 mm were cut out of polymer sheet H. The larger cut sheet was folded with the two smaller sheets interposed in the center of the fold in the same manner as in the preparation of absorbent member A to obtain absorbent member E.

8) Preparation of Absorbent Member F

An aqueous slurry of chemical wood pulp having a centrifugal water retention of 1.3 g/g (Skeena Prime, available from Skeena Cellulose Co.) was made into a web on a papermaking net and dried to obtain wet-processed absorbent paper having a Klemm's water absorption of 30 mm and a basis weight of 18 g/m². The resulting absorbent paper was cut into a size of 70 mm by 175 mm. Superabsorbent polymer B was substantially uniformly scattered all over the absorbent paper in an amount of 40 g/m². The same chemical wood pulp as used in absorbent member E (centrifugal water retention: 1.1 g/g) was air-laid all over the polymer layer in an amount of 200 g/m². The resulting laminate having the absorbent paper, the superabsorbent polymer B layer and the pulp layer was wrapped in a 140 mm wide and 175 mm long cut sheet of the above-described wet-processed absorbent paper and compressed into a unitary body to obtain absorbent member F.

9) Preparation of Absorbent Member G

The same chemical wood pulp used in absorbent member F (centrifugal water retention: 1.3 g/g) and crosslinked pulp A used in absorbent member B were mixed at a ratio of 80:20 and uniformly dispersed in water. The slurry was made into a web on a papermaking net and dried to obtain wet-processed absorbent paper having a Klemm's water absorption of 35 mm and a basis weight of 45 g/m². Separately, the same slurry as used above was made into a web having a dry basis weight of 45 g/m² on a papermaking net, and superabsorbent polymer B was uniformly scattered thereon in an amount of 10 g/m² while the web was wet. The previously prepared wet-processed absorbent paper was superposed on (Fibribond, available from Sansho K.K.) at a ratio of 97:3 was made into a web on a papermaking net and dried to obtain wet-processed nonwoven fabric A having a Klemm's water absorption of 50 mm and a basis weight of 35 g/m². The wet-processed nonwoven fabric A is to be used as an inner fiber layer.

The same slurry was made into a web having a dry basis weight of 25 g/m² on a papermaking net, and superabsorbent polymer A was uniformly scattered thereon in an amount of 40 g/m² while the web was wet. Wet-processed nonwoven fabric A (inner fiber layer) was superposed on the scattered polymer, and the laminate was compression dried in a drier to obtain polymer sheet F having a total basis weight of 100 g/m².

An aqueous slurry of crosslinked pulp A, crosslinking pulp B, and the same polyvinyl alcohol fiber as used above at a ratio of 87:10:3 was made into a web on a papermaking net and dried to obtain wet-processed nonwoven fabric B having a Klemm's water absorption of 55 mm and a basis weight of 30 g/m².

The same aqueous slurry as used for the preparation of nonwoven fabric B was made into a web having a dry basis weight of 20 g/m² on a papermaking net. Superabsorbent polymer A was uniformly scattered on the web while wet in an amount of 50 g/m². Wet-processed nonwoven fabric B was superposed on the polymer A, and the laminate was compression dried in a drier to obtain polymer sheet G having a total basis weight of 100 g/m².

Polymer sheet F was cut into a piece having a size of 140 mm by 175 mm, and polymer sheet G was cut into two pieces each having a size of 35 mm by 80 mm. The cut sheet of polymer sheet F was folded with two cut sheets of polymer sheet G being interposed in the center of the fold in the same manner as in the preparation of absorbent member A. The same suction heat-bond nonwoven fabric as used in absorbent member A (surface fiber layer, Klemm's water absorption: 10 mm) was cut into a size of 70 mm by 175 mm, and the cut sheet was superposed on the wearer-facing side of the folded polymer sheet F to prepare absorbent member D.

7) Preparation of Absorbent Member E

TABLE 1

| Absorbent Member | Hydrophilic Fiber | Superabsorbent Polymer | Hydrophilic Fiber Content (wt %) | Polymer Content (wt %) | Diffusion Gradient in Fiber Aggregate | Thickness (mm) Central Portion | Thickness (mm) Surrounding Portion | Effective Volume $V_0$ (cm³) | Physiological Saline Retention $V_1$ (g) | P ($V_1/V_0$) |
|---|---|---|---|---|---|---|---|---|---|---|
| A | PE/PET conjugate fiber/PE fiber | A | 65 | 35 | made | 1.8 | 1.1 | 15.4 | 41.7 | 2.7 |
| B | PE/PET conjugate fiber/PE fiber | A | 62 | 38 | made | 1.5 | 1.5 | 18.4 | 49.5 | 2.7 |
| C | PE/PET conjugate fiber/crosslinked pulp | A | 56 | 37 | made | 2.3 | 1.4 | 19.1 | 42.1 | 2.2 |
| D | PE/PET conjugate fiber/crosslinked pulp/PE fiber | A | 63 | 37 | made | 2 | 1.2 | 16.9 | 40.5 | 2.4 |
| E | chemical wood pulp | A | 0 | 45 | not made | 2 | 1.2 | 16.9 | 47.1 | 2.8 |
| F | chemical wood pulp | B | 0 | 16 | not made | 3.1 | 3.1 | 38 | 18.1 | 0.5 |
| G | crosslinked pulp/chemical wood pulp | B | 18 | 10 | not made | 1.8 | 1.1 | 15.4 | 11.2 | 0.7 |

TABLE 1-continued

| Absorbent Member | Hydrophilic Fiber | Super-absorbent Polymer | Hydrophilic Fiber Content (wt %) | Polymer Content (wt %) | Diffusion Gradient in Fiber Aggregate | Thickness (mm) Central Portion | Thickness (mm) Surrounding Portion | Effective Volume $V_0$ (cm$^3$) | Physiological Saline Retention $V_1$ (g) | P ($V_1/V_0$) |
|---|---|---|---|---|---|---|---|---|---|---|
| H | PE/PET conjugate fiber/chemical wood pulp | B | 10 | 3 | made | 5 | 5 | 61.3 | 6.9 | 0.1 | the polymer B layer, and the laminate was compressed and dried into a unitary body to obtain a polymer sheet having a total basis weight of 100 g/m$^2$. Two sheets of 35 mm in width and 80 mm in length and a sheet of 140 mm in width and 175 mm in length were cut out of the resulting polymer sheet. The two sheets of smaller size were wrapped in the sheet of larger size in the same manner as in the preparation of absorbent member A to obtain absorbent member G.

10) Preparation of Absorbent Member H

A uniform aqueous slurry of the same chemical wood pulp as used in absorbent member F (centrifugal water retention: 1.3 g/g) was made into a web on a papermaking net and dried to obtain wet-processed absorbent paper having a Klemm's water absorption of 30 mm and a basis weight of 18 g/m$^2$. The absorbent paper was cut into a size of 70 mm by 175 mm, and 10 g/m$^2$ of superabsorbent polymer B was uniformly scattered all over the absorbent paper. The same chemical wood pulp as used in absorbent member E (centrifugal water retention: 1.1 g/g) was air-laid all over the polymer B layer in an amount of 300 g/m$^2$. The resulting laminate of the absorbent paper, the polymer B layer, and the pulp layer was wrapped in a 140 mm wide and 175 mm long cut sheet of the same suction heat-bond nonwoven fabric as used in absorbent member A (Klemm's water absorption: 10 mm; basis weight: 20 g/m$^2$) and compressed into a unitary body to obtain absorbent member H.

The particulars of absorbent members A to H prepared above are summarized in Table 1 below. Table 1 show the kinds of the hydrophilic fiber and the superabsorbent polymer used, the content of the non-swelling hydrophilic fiber or low-swelling hydrophilic fiber (centrifugal water retention: 0.7 g/g or less) (shown under the heading "Hydrophilic Fiber Content"), the superabsorbent polymer content, the presence or absence of a diffusion gradient (or a Klemm's water absorption gradient) in the fiber aggregate from the surface of the absorbent member to the superabsorbent polymer, the thickness of the central portion (thicker portion in some absorbent members), the thickness of the other portion (the portion surrounding the central portion), the effective volume $V_0$, the physiological saline retention $V_1$, and the retention-to-volume ratio P ($=V_1/V_0$).

The centrifugal water retention of the hydrophilic fiber or foam, the thickness of the absorbent member, and the effective volume $V_0$, the physiological saline retention $V_1$ and the retention-to-volume ratio P of the absorbent member were measured as follows.

1) Centrifugal Water Retention

Measurement was carried out in a room maintained at 20° C. and 65% RH. A sample of a hydrophilic fiber or foam precisely weighing 1 g was put in a nylon mesh bag (250 mesh), and the bag was put in a beaker containing 500 ml of ion-exchanged water and left to stand for 30 minutes. The bag was taken out of water and centrifuged on a centrifuge (H-130C, manufactured by Kokusan Enshinki K.K.) at 2000 rpm (centrifugal acceleration: 895 G) for 10 minutes. The sample was weighed to obtain a water retention after centrifugation (centrifugal water retention) according to the following equation:

Centrifugal water retention (g/g)=[weight of sample after centrifugation−initial weight of sample]/initial weight of sample The centrifugal physiological saline retention of superabsorbent polymer A or B was measured in the same manner as for centrifugal water retention, except for replacing ion-exchanged water with physiological saline (supplied by OTSUKA PHARMACEUTICAL CO., LTD). Because the superabsorbent polymer takes up moisture under the above-described room conditions to gain in weight, the initial sample weight was measured immediately after the sample was taken out of a closed container.

2) Thickness

A disk having an area of 3 cm$^2$ (radius: 9.8 mm) was put on an absorbent member to give a load of 2.5 g/cm$^2$, and the thickness L of the absorbent member was measured with a thickness meter (Peacock Dial Gauge, supplied by Ozaki Seisakusho K.K.).

3) Effective Volume $V_0$

The effective volume $V_0$ (cm$^3$) of an absorbent member was obtained by multiplying the thickness L (cm) under load (2.5 g/cm$^2$) by the effective area (cm$^2$) of the absorbent member.

4) Physiological Saline Retention $V_1$ and Retention-to-volume Ratio P

Measurement was carried out in a room maintained at 20° C. and 65% RH. An absorbent member was put in a nylon mesh bag (250 mesh), and the bag was put in a beaker containing 3000 ml of physiological saline (supplied by OTSUKA PHARMACEUTICAL CO., LTD) and left to stand for 30 minutes. The bag was taken out of the beaker and centrifuged on a centrifuge (H-130C, manufactured by Kokusan Enshinki K.K.) at 2000 rpm (centrifugal acceleration: 895 G) for 10 minutes. The dewatered sample was weighed to obtain a physiological saline retention after centrifugation (physiological saline retention) according to the following equation:

Physiological saline retention $V_1$ (g)=weight of sample after centrifugation (g)−initial weight of sample (g)

The physiological saline retention $V_1$ (g) was divided by the effective volume $V_0$ (cm$^3$) of the absorbent member to give a retention-to-volume ratio P (g/cm$^3$).

EXAMPLES 1 TO 4 AND COMPARATIVE EXAMPLES 1' TO 4'

Absorbent articles 1 to 4 according to the first aspect of the present invention and comparative absorbent articles 1 to 4' were prepared by using absorbent members A to H.

a) Preparation of Absorbent Article 1

Perforated nonwoven fabric which was suction heat-bond nonwoven fabric made of PET/PE core/sheath type conjugated fiber having a basis weight of 25 g/m² and having perforations at an opening area ratio of 10%, each perforation having a diameter of 0.8 mm, was superposed as a topsheet 2 on absorbent member A as an absorbent member 4 as shown in FIGS. 1 and 2. The laminate was passed through heat rolls having a pattern 12 shown in FIG. 1 to make a heat-sealed unitary structure. Doubled spun-bond nonwoven fabric made of PET/PE core/sheath type conjugate fiber having a basis weight of 20 g/m² was superposed as a leakproof sheet 6 on each side of the topsheet 2 and heat-sealed through heat rolls (heat sealing 11). A hot-melt adhesive 5 was applied to the central portion of the reverse side (opposite to the wearer-facing side) of the absorbent member 4 in a helical pattern (width: 50 mm; length: 150 mm) in an amount of 5 g/m² and to each longitudinal side of the central portion in a beads pattern (width: 1 mm; length: 150 mm) in an amount of 150 g/m². A polyethylene backsheet 3 having a basis weight of 25 g/m² was adhered to the absorbent member 4 via the hot-melt adhesive 5. The periphery of the absorbent member 4 was heat-sealed (heat sealing 13) to join the leakproof sheet 6, the topsheet 2, and the backsheet 3 together, followed by trimming into the shape shown in FIG. 1 having a width of 95 mm and a length of 200 mm. A hot-melt pressure-sensitive adhesive was applied to the back of the backsheet 3 in two bands each having a width of 20 mm and a length of 150 mm in an amount of 30 g/m² to form a sticking area 7. The sticking area 7 was covered with a 60 mm wide and 170 mm long release sheet 8 to complete an absorbent article (sanitary napkin) 1.

b) Preparation of Absorbent Articles 2 to 4 and Comparative Absorbent Articles 1' to 4'

Absorbent articles 2 to 4 according to the present invention were prepared in the same manner as for absorbent article 1, except for replacing absorbent member A with absorbent members B to D. Comparative absorbent articles 1' to 4' were prepared in the same manner, except for using absorbent members E to H in place of absorbent member A.

The liquid fixing ratio (i.e., physiological saline fixing ratio when an absorbent member absorbs 10 g of physiological saline and, after 5 minutes of absorption, is dewatered by centrifugation), leakproofness and anti-back-flow property of the resulting absorbent articles were evaluated in accordance with the following methods. The results obtained are shown in Table 2.

i) Liquid Fixing Ratio

Measurement was made in a room kept at 20° C. and 65% RH. An acrylic resin plate 15 shown in FIGS. 3A and 3B having a hole of 10 mm in diameter was put on a horizontally placed absorbent article as shown in FIG. 4. Two weights 16 and 16 were put on the plate 15 to apply a load of 5 g/cm² to the absorbent article. Ten grams of physiological saline (available from Otsuka Pharmaceutical Co., Ltd.) in a 10 ml beaker was poured into the hole in about 2 seconds. After the liquid was completely absorbed, the absorbent article was left to stand for 5 minutes with the acrylic resin plate 15 on. Then, the absorbent article was put in a nylon mesh bag (250 mesh) whose size was enough to have the absorbent article without a bend. The bag was set in a centrifuge (H-130C, manufactured by Kokusan Enshinki K.K.) with the topsheet side of the sample facing outward so that the centrifugal acceleration might be imposed from the absorbent member toward the topsheet side thereby to separate the physiological saline that was not completely fixed in the absorbent member. The sample was dewatered by centrifugation at 2000 rpm (centrifugal acceleration: 895 G) for 10 minutes and then weighed to obtain a liquid fixing ratio according to the following equation:

$$\text{Liquid fixing ratio } (\%) = [(C-A)/(B-A)] \times 100$$

wherein A is the initial weight (g) of an absorbent article; B is the weight (g) of the absorbent article after pouring 10 g of physiological saline; and C is the weight (g) of the absorbent article after centrifugation.

ii) Leakproofness (Occurrence of Leaks)

Figure 5A:
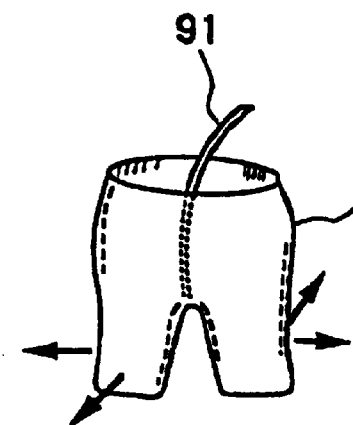
FIGS. 5A and 5B illustrate a method of evaluating leakproofness.
Figure 5B:
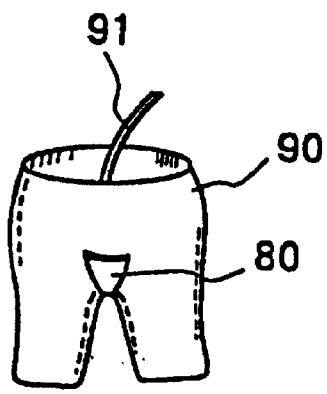

As shown in FIG. 5B, an absorbent article 80 was fitted to a movable model 90 of female hips and crotch by use of sanitary panties. As shown in FIG. 5A, the model 90 was made to take a walking movement at a rate of 100 steps/min for 10 minutes. While keeping the model in a moving mode, 5 g of defibrinated horse blood (available from Nihon Biotest Kenkyusho K.K.) was poured through a tube 91 at a rate of 4 g/min, and the walking movement was continued for an additional 20 minute period at the same speed. Three grams of defibrinated horse blood was further poured at a rate of 4 g/min (8 g in total) in a moving mode, followed by 20 minute walking movement. Another 3 g of defibrinated horse blood was poured (11 g in total), followed by another 20 minute walking movement. The test was conducted 10 times, and the number of samples having a leak out of 10 was counted after 5 g-absorption followed by 20 minute-walking, after 8 g-absorption followed by 20 minute-walking, and after 11 g-absorption followed by 20 minute-walking.

iii) Measurement of Back-flow

Figure 3A:
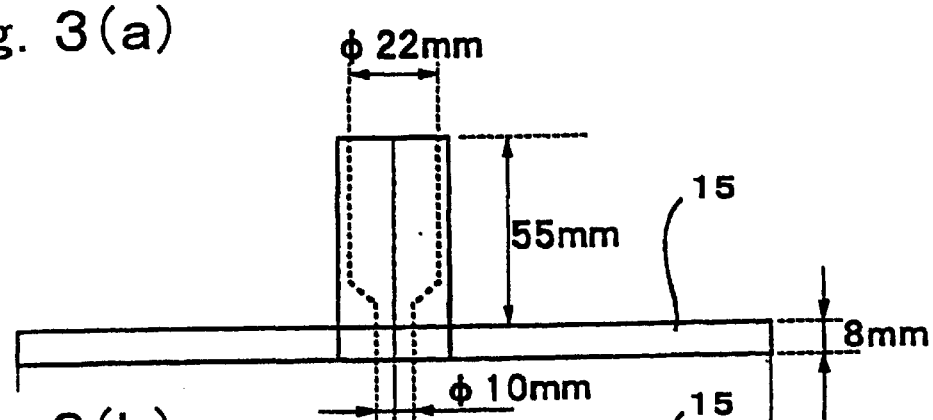
FIG. 3A is a side view of an acrylic resin plate used in the measurement of liquid fixing ratio and back-flow.
Figure 3B:
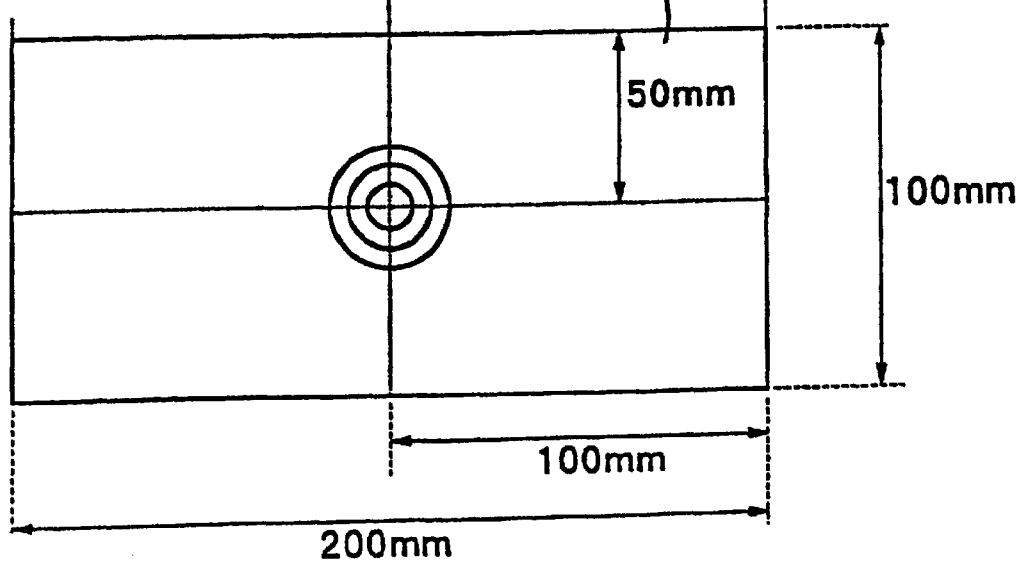
FIG. 3B is a plane view of the acrylic resin plate of FIG. 3A.
Figure 4:
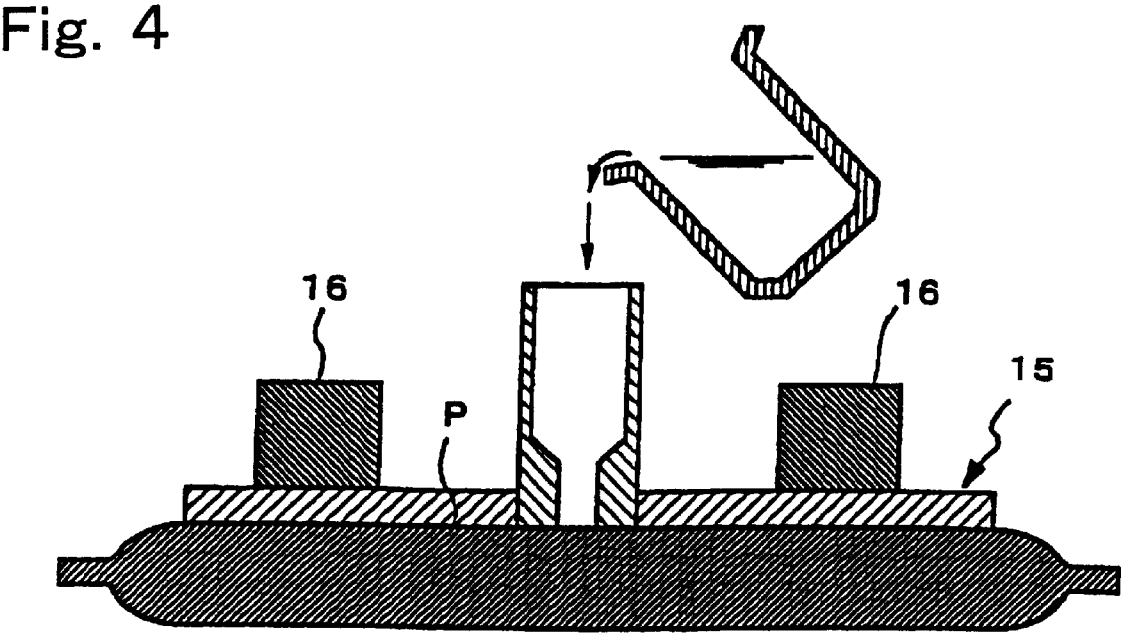
FIG. 4 illustrates a method of measuring liquid fixing ratio and back-flow.

An acrylic resin plate 15 shown in FIGS. 3A and 3B having a hole of 10 mm in diameter was put on a horizontally placed absorbent article as shown in FIG. 4. Two weights 16 and 16 were put on the plate 15 to apply a load of 5 g/cm² to the absorbent article. Six grams of defibrinated horse blood (available from Nihon Biotest Kenkyusho K.K.) was poured from a 10 ml beaker through the hole in about 2 seconds. After the liquid was completely absorbed, the absorbent article was left to stand for 5 minutes with the acrylic plate 15 on. Then, a stack of 10 sheets of absorbent paper 100% made of chemical softwood pulp having a basis weight of 30 g/m² (75 mm wide and 195 mm long) was placed on the wearer-facing side of the sanitary napkin. The sanitary napkin with paper on was fitted to the movable model 90 shown in FIG. 5 by using sanitary panties. The model 90 was made to take a walking movement at a rate of 100 steps/min for 10 minutes.

After the walking movement, the sanitary napkin 80 and 10 sheets of absorbent paper were removed, and the weight of blood absorbed into the absorbent paper was measured as a back-flow (g). The test was conducted 5 times to obtain an average.

TABLE 2

| Sample | Absorbent Member | Liquid Fixing Ratio (%) | Number of Leaky Samples | | | Back-flow (g) |
|---|---|---|---|---|---|---|
| | | | 5 g | 8 g | 11 g | |
| 1 | A | 97 | 0 | 0 | 0 | 0.05 |
| 2 | B | 93 | 0 | 0 | 3 | 0.1 |
| 3 | C | 92 | 0 | 0 | 4 | 0.2 |
| 4 | D | 96 | 0 | 0 | 0 | 0.1 |
| 1' | E | 78 | 0 | 2 | 8 | 0.5 |
| 2' | F | 58 | 0 | 5 | 10 | 0.5 |

TABLE 2-continued

| Sample | Absorbent Member | Liquid Fixing Ratio (%) | Number of Leaky Samples 5 g | 8 g | 11 g | Back-flow (g) |
|---|---|---|---|---|---|---|
| 3' | G | 53 | 1 | 7 | 10 | 1.8 |
| 4' | H | 38 | 0 | 3 | 8 | 0.8 |

As shown in Tables 1 and 2, the absorbent articles 1 to 4 according to the present invention comprise non-swelling hydrophilic fiber or low-swelling hydrophilic fiber (having a centrifugal water retention of 0.7 g/g or less) and a superabsorbent polymer and have a liquid fixing ratio of 90% or more (i.e., 90% or more of absorbed physiological saline can be fixed completely), leaving little free liquid. As a result, the absorbent articles of the invention, while of thin type, ensure a wearer a comfort while worn, causing little leakage, little back-flow, and with no stickiness nor stuffiness. Such excellent performance is attributed to an ideally designed flow of liquid from absorption into the topsheet till arrival to a superabsorbent polymer, which is realized by using a specifically designed combination of specific hydrophilic fiber and the superabsorbent polymer.

To the contrary, the comparative samples 1' to 4' have a low liquid fixing ratio (80% or less) and cause considerable leakage and back-flow.

EXAMPLE 5

An absorbent article according to the first and second aspects of the present invention, designated absorbent article 5, was prepared in the same manner as for absorbent article 1, except for replacing the moisture-impermeable backsheet with a porous moisture-permeable backsheet obtained by molding a molten mixture of 50% calcium carbonate and 50% polyethylene into a film and biaxially stretching the film. The porous backsheet had a moisture vapor transport rate of 1.7 g/(100 cm$^2$·hr).

EXAMPLE 6

An absorbent article according to the first and second aspects of the present invention, designated absorbent article 6, was prepared in the same manner as for absorbent article 4, except for replacing the moisture-impermeable backsheet with the same porous moisture-permeable backsheet used in Example 5 (moisture vapor transport rate: 1.7 g/(100 cm$^2$·hr)).

COMPARATIVE EXAMPLE 5'

A comparative absorbent article, designated absorbent article 5', was prepared in the same manner as for absorbent article 4', except for replacing the moisture-impermeable backsheet with the same porous moisture-permeable backsheet used in Example 5 (moisture vapor transport rate: 1.7 g/(100 cm$^2$·hr)).

In order to examine an inhibitory effect on temperature and humidity rise during use, the absorbent articles prepared in Examples 5 and 6 and Comparative Examples 4' and 5' were tested as follows.

iv) Effect on Temperature and Humidity Rise

The test was carried out in a room kept at 30° C. and 65% RH. A person naked to the waist lay motionless on his or her stomach for 30 minutes in the room. An absorbent article having absorbed 3 g of physiological saline in the central portion thereof was put on the person's back with the topsheet side down. A probe of a temperature-humidity sensor (main body: Data Stocker TRH-DM2; sensor: exclusive probe THP-28; both supplied by Shinyie Kaisha) was set between the absorbent article and the skin, and all the edges of the absorbent article were sealed with adhesive tape so as not to allow water vapor to escape. After the person kept motionless for an additional 2 hour period, the temperature and the humidity between the sample and the skin were read. The results obtained are shown in Table 3.

TABLE 3

| Sample | Absorbent Member | Backsheet | Liquid Fixing Ratio (%) | After 2 hrs. Temp. (° C.) | Humidity (%) |
|---|---|---|---|---|---|
| 5 | A | moisture permeable | 97 | 35.5 | 70 |
| 6 | D | moisture permeable | 96 | 35.6 | 71 |
| 4' | H | moisture permeable | 38 | 36.5 | 96 |
| 5' | H | moisture permeable | 38 | 36.1 | 85 |

As can be seen from Table 3, the humidity reached 96% in comparative absorbent article 4' which uses a moisture impermeable backsheet and has a low liquid fixing ratio. Even with the moisture impermeable backsheet replaced with a moisture permeable one (comparative example 5'), the reduction of humidity was only about 10%. On the other hand, absorbent articles 5 and 6 according to the present invention which use a moisture permeable backsheet and have a high liquid fixing ratio successfully decrease the humidity to about 70% and also control the temperature rise. It has now been understood that the present invention provides an absorbent article which ensures a wearer a comfort with suppressed rises in temperature and humidity while worn.

EXAMPLES 7 AND 8 AND COMPARATIVE EXAMPLES 6' AND 7'

An absorbent article according to the first and second aspects of the present invention, designated absorbent articles 7 and 8, and comparative absorbent articles 6' and 7' were prepared in the same manner as for absorbent article 1 (Example 1), except for replacing absorbent member A and the moisture impermeable backsheet with the following absorbent member and moisture permeable backsheet, respectively.

| Sample | Absorbent Member | Moisture Permeable Backsheet | Remark |
|---|---|---|---|
| 7 | D | A | invention |
| 8 | D | B | invention |
| 6' | F | A | comparison |
| 7' | F | C | comparison |

Moisture permeable backsheets A to C were biaxially stretched films which were prepared from a polyethylene/calcium carbonate mixture containing different dispersants for uniformly dispersing calcium carbonate in polyethylene so as to have different moisture vapor transport rate and/or wetting tensions as shown in Table 4 below. The moisture vapor transport rate is measured in accordance with JIS Z0208. The wetting tension was measured as follows.

v) Measurement of Wetting Tension

The wetting tension of a moisture permeable backsheet was measured as follows with reference to JIS K6768 "Plastics—film and sheeting—determination of wetting tension".

The measurement was made in a room kept at 23° C. and 50% RH. A 100 mm wide and 200 mm long specimen was cut out of a sample sheet. The specimen is not limited to that size as long as it can receive a test liquid at three points apart. Commercially available test liquids prepared from two reagents—formaldehyde and ethylene glycol monoethyl ether—having a surface tension adjusted between 30 and 50 mN/m (available from Wako Pure Chemical Industry Co., Ltd.) were used.

Figure 6:
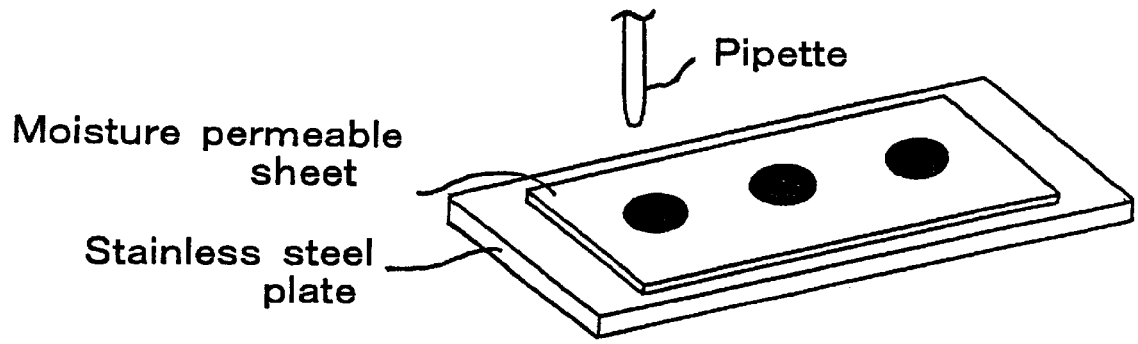
FIG. 6 illustrates a method of measuring wetting tension.

As shown in FIG. 6, the specimen was placed on a horizontal stainless steel plate 150 mm in width and 250 mm in length. A test liquid having a surface tension of 50 mN/m was pipetted on three points of the specimen in an amount of about 1 ml each and allowed to stand for 3 minutes. The specimen was removed to examine whether the test liquid had oozed to the stainless steel plate side through the specimen.

When oozing was not observed at all the three points, the same test was performed using a test liquid having a surface tension of 49 mN/m. When no oozing occurred yet, the same test was repeated with the surface tension of the test liquid decreased by 1 mN/m until oozing occurred at at least one point out of three.

The lowest surface tension of test liquids applied that did not ooze through the specimen was taken as a wetting tension of the test sheet. For example, in case when the specimen did not allow a test liquid having a surface tension of 40 mN/m to ooze and allowed a test liquid having a surface tension of 39 mN/m to ooze for the first time, the 40 mN/m was taken as a wetting tension of the sheet.

TABLE 4

| Moisture Permeable Backsheet | Basis Weight (g/m$^2$) | Moisture Vapor Transport Rate (g/(100 cm$^2$ · hr)) | Wetting Tension (mN/m) |
|---|---|---|---|
| A | 35 | 1.9 | 35 |
| B | 39 | 1.9 | 42 |
| C | 39 | 1.3 | 40 |

The liquid fixing ratio (fixing ratio of physiological saline) of absorbent articles 7 and 8 (Examples 7 and 8) and absorbent articles 6' and 7' (Comparative Examples 6' and 7') was measured by the above-described method. The results obtained are shown in Table 5 below. Further, these absorbent articles were evaluated for resistance against oozing through their backsheet according to the test method described below.

vi) Resistance to Oozing

Figure 7A:
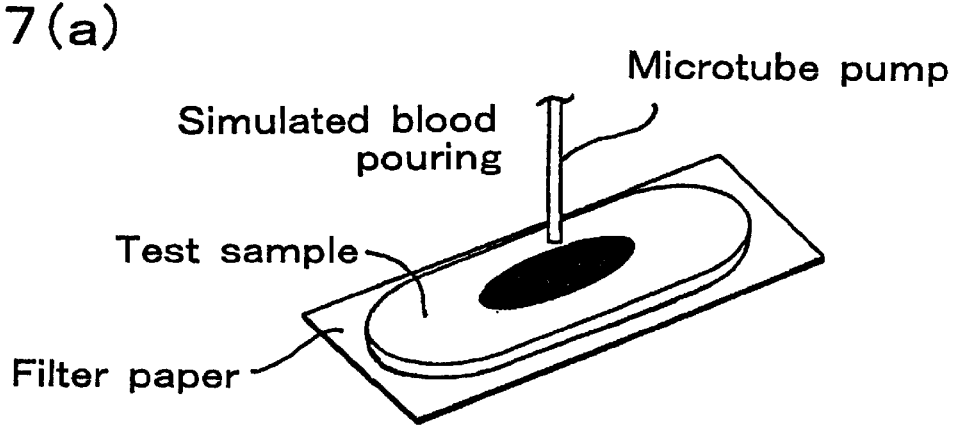
FIGS. 7A and 7B illustrate a method of evaluating resistance to oozing.

The test was performed in an environment of 20° C. and 65% RH. As shown in FIG. 7A, an absorbent article (sanitary napkin) was put on a 100 mm wide and 230 mm long cut sheet of filter paper (Type 2, available from Toyo Roshi K.K.). Ten grams of simulated blood having a surface tension of 35 mN/m was poured on the center of the napkin by means of a microtube pump at a rate of 10 g/min, and the sample was left to stand for 1 minute.

Figure 7B:
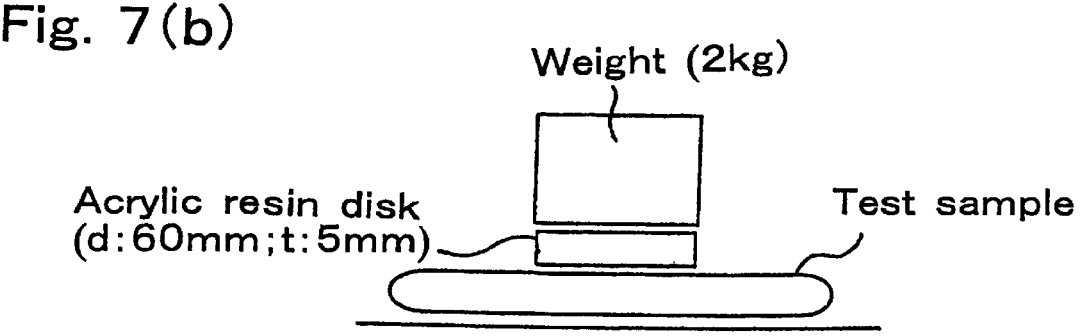

Then, as shown in FIG. 7B, an acrylic resin disk having a diameter of 60 mm and a thickness of 5 mm was put on the central portion of the sample having absorbed simulated blood, and a 2 kg weight was further put thereon to press the sample. Whether or not the simulated blood oozed to stain the filter paper was observed with the naked eye after 30 minutes, 1 hour and 3 hours from the start of pressing. The results are shown in Table 5.

The simulated blood having a surface tension of 35 mN/m was prepared as follows. In 1500 g of ion-exchanged water was completely dissolved 5.3 g of carboxymethyl cellulose sodium (CMC·Na, available from Kanto Kagaku K.K.). Separately, 27 g of sodium chloride and 12 g of sodium hydrogencarbonate were completely dissolved in 556 g of ion-exchanged water. The resulting two solutions and 900 g of glycerol were mixed up by stirring, and 0.3 g of Red 2 (available from Hodogaya Chemical Co., Ltd.) was completely dissolved therein. To the mixture was further added 0.432 g of an alkyl glucoside surface active agent (AG-10L, available from Kao Corp.) to give a surface active agent concentration of 0.015%. The resulting solution was maintained at 20° C., and its surface tension was confirmed to be within 35±1 mN/m before use. If the surface tension was out of that range, the concentration of the alkyl glucoside was increased or decreased to adjust the surface tension to 35±1 mN/m.

TABLE 5

| Sample | Absorbent Member | Moisture Permeable Backsheet | Liquid Fixing Ratio (%) | Oozing 30 mins | 1 hr | 3 hrs |
|---|---|---|---|---|---|---|
| 7 | D | A | 96 | not observed | not observed | not observed |
| 8 | D | B | 96 | not observed | not observed | observed |
| 6' | F | A | 58 | not observed | observed | observed |
| 7' | F | C | 58 | observed | observed | observed |

As shown in Table 5 above, comparative absorbent articles 6' and 7' caused oozing through the backsheet. It is seen that a body fluid, if it has a low surface tension, oozes out through the backsheet when the absorbent article has a liquid fixing ratio of less than 90% or when the wetting tension of the backsheet is higher than 37 mN/m. On the other hand, the absorbent article 7 and 8 of the invention causes no oozing even when pressed for 1 hour. It has now been understood that the absorbent article having a backsheet whose wetting tension is 37 mN/m exhibits satisfactory breathability and yet satisfactorily prevents body fluids from oozing through its backsheet even when the body fluids have a low surface tension.

The absorbent article according to the first aspect of the present invention hardly causes leakage or stuffiness and gives a comfort to a wearer even when a large amount of a body fluid is discharged and exhibits high absorptivity and excellent leakproofness.

The absorbent article is capable of completely immobilizing most of the liquid it absorbs even when the amount of the liquid discharged is large. For this, the absorbent article ensures a wearer a comfort while worn by reducing humidity and temperature rises, stuffiness, and stickiness due to back-flow of the liquid. Where a moisture permeable sheet is used as a leakproof backsheet, humidity and temperature rises which may result from perspiration can be suppressed effectively to further improve the comfort. Since the hydrophilic material itself, which is used in the absorbent member, retains no or little liquid, the void structure, i.e., the interstices among the individual fibers or voids among foamed particles, where a body fluid is liable to stay, can be held stable. In addition, because this void structure facilitates and accelerates diffusion of an absorbed body fluid toward the superabsorbent polymer particles, most of the absorbed liquid can be led to the superabsorbent polymer and completely retained therein.

The absorbent article according to the second aspect of the invention hardly causes stuffiness and gives a comfort to a wearer even when worn for a long time and exhibits high absorptivity and excellent leakproofness.

Having a certain high liquid fixing ratio, the absorbent article does not invite stuffiness due to water vapor generation from the absorbent layer nor causes leaks due to back-flow of the absorbed liquid from the absorbent layer while worn. The backsheet having a breathability further secures prevention of stuffiness in the internal environment.

Further, in the case that the absorbent article has a backsheet whose wetting tension is 37 mN/m or lower, the absorbed body fluid can effectively be prevented from oozing through the backsheet even when the body fluid has a low surface tension, thus providing a wearer with more comfort and assured feeling while worn.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising a liquid permeable topsheet, a liquid impermeable backsheet, and a liquid retentive absorbent layer, wherein said absorbent layer comprises a superabsorbent polymer and hydrophilic fiber or foam that does not swell with water or hydrophilic fiber or foam that has a water retention of 0.7 g/g or less when it is swollen with water and then dewatered by centrifugation, and said absorbent article has a physiological saline fixing ratio of 90% or more when it absorbs 10 g of physiological saline and, after 5 minutes, is dewatered by centrifugation.

2. The absorbent article according to claim 1, wherein said absorbent layer has a thickness of 2.5 mm or smaller and has a $V_1/V_0$ ratio of 1 g/cm$^3$ or higher, wherein $V_0$ is the effective volume (cm$^3$) of said absorbent layer, and $V_1$ is the amount (g) of physiological saline retained when said absorbent layer is swollen with physiological saline and dewatered by centrifugation.

3. The absorbent article according to claim 1, wherein said backsheet is breathable.

4. The absorbent article according to claim 1, wherein the content of said hydrophilic fiber or foam that does not swell with water or said hydrophilic fiber or foam that has a water retention of 0.7 g/g or less in said absorbent layer is 30 to 70% by weight, and said superabsorbent polymer is three-dimensionally dispersed in an aggregate of said hydrophilic fiber or in said hydrophilic foam.

5. The absorbent article according to claim 1, wherein said absorbent layer has a thicker portion in the area where a body fluid is to be discharged, said thicker portion has a thickness of 1.5 to 2.5 mm, and the portion surrounding said thicker portion has a thickness of 0.5 to 2.0 mm.

6. The absorbent article according to claim 1, wherein said absorbent layer comprises a surface fiber layer, which forms the surface in contact with the topsheet, and an inner fiber layer, which is disposed on the back side of the surface fiber layer and which contains the superabsorbent polymer or is in contact with the superabsorbent polymer, and wherein said surface fiber layer having a lower Klemm's water absorption than said inner fiber layer.

7. An absorbent article comprising a liquid permeable topsheet, a liquid impermeable backsheet, and a liquid retentive absorbent layer, wherein said backsheet is breathable, and said absorbent article has a physiological saline fixing ratio of 90% or more when it absorbs 10 g of physiological saline and, after 5 minutes, is dewatered by centrifugation.

8. The absorbent article according to claim 7, wherein said backsheet has a wetting tension of 37 mN/m or lower.

9. The absorbent article according to claim 7, wherein said absorbent layer comprises a superabsorbent polymer and hydrophilic fiber or foam that does not swell with water or hydrophilic fiber or foam that has a water retention of 0.7 g/g or less when it is swollen with water and then dewatered by centrifugation.

* * * * *

UNITED STATES PATENT AND TRADEMARK OFFICE
CERTIFICATE OF CORRECTION

PATENT NO.        : 6,506,959 B2
APPLICATION NO.   : 09/819725
DATED             : January 14, 2003
INVENTOR(S)       : Mitsugu Hamajima et al.

It is certified that error appears in the above-identified patent and that said Letters Patent is hereby corrected as shown below:

At column 13, line 3, change "polyvinyl alcohol fiber." to read:

--polyvinyl alcohol fiber (Fibribond, available from Sansho K.K.) at a ratio of 97:3 was made into a web on a papermaking net and dried to obtain wet-processed nonwoven fabric A having a Klemm's water absorption of 50 mm and a basis weight of 35 g/m$^2$. The wet-processed nonwoven fabric A is to be used as an inner fiber layer.

The same slurry was made into a web having a dry basis weight of 25 g/m$^2$ on a papermaking net, and superabsorbent polymer A was uniformly scattered thereon in an amount of 40 g/m$^2$ while the web was wet. Wet-processed nonwoven fabric A (inner fiber layer) was superposed on the scattered polymer, and the laminate was compression dried in a drier to obtain polymer sheet F having a total basis weight of 100 g/m$^2$.

An aqueous slurry of crosslinked pulp A, crosslinking pulp B, and the same polyvinyl alcohol fiber as used above at a ratio of 87:10:3 was made into a web on a papermaking net and dried to obtain wet-processed nonwoven fabric B having a Klemm's water absorption of 55 mm and a basis weight of 30 g/m$^2$.

The same aqueous slurry as used for the preparation of nonwoven fabric B was made into a web having a dry basis weight of 20 g/m$^2$ on a papermaking net. Superabsorbent polymer A was uniformly scattered on the web while wet in an amount of 50 g/m$^2$. Wet-processed nonwoven fabric B was superposed on the polymer A, and the laminate was compression dried in a drier to obtain polymer sheet G having a total basis weight of 100 g/m$^2$.

Polymer sheet F was cut into a piece having a size of 140 mm by 175 mm, and polymer sheet G was cut into two pieces each having a size of 35 mm by 80 mm. The cut sheet of polymer sheet F was folded with two cut sheets of polymer sheet G being interposed in the center of the fold in the same manner as in the preparation of absorbent member A. The same suction heat-bond nonwoven fabric as used in absorbent member A (surface fiber layer, Klemm's water absorption: 10 mm) was cut Signed and Sealed this
Twenty-ninth Day of November, 2011

David J. Kappos
*Director of the United States Patent and Trademark Office* into a size of 70 mm by 175 mm, and the cut sheet was superposed on the wearer-facing side of the folded polymer sheet F to prepare absorbent member D.

7) Preparation of Absorbent Member E--.

At column 14, line 5, after "superposed on", delete "(Fibribond, available from Sansho K.K.) at a".

At column 14, delete lines 6-45 in their entirety.